United States Patent
Banegas

(10) Patent No.: US 7,267,126 B1
(45) Date of Patent: Sep. 11, 2007

(54) PORTABLE COMPACT DENTAL HYGIENE KIT

(76) Inventor: Shawn J. Banegas, 83 Viejas Grade Rd., Alpine, CA (US) 91901

( * ) Notice: Subject to any disclaimer, the term of this patent is extended or adjusted under 35 U.S.C. 154(b) by 368 days.

(21) Appl. No.: 11/098,632

(22) Filed: Apr. 5, 2005

(51) Int. Cl.
*A45D 44/18* (2006.01)

(52) U.S. Cl. ..................................... 132/309

(58) Field of Classification Search ............... 132/308, 132/309, 311, 325; 206/389, 397, 405, 406; 15/167.1, 167.2
See application file for complete search history.

(56) References Cited

U.S. PATENT DOCUMENTS

| | | | | |
|---|---|---|---|---|
| 1,062,961 A | * | 5/1913 | Funcke | 132/308 |
| 1,473,766 A | * | 11/1923 | Healy | 132/309 |
| 1,659,628 A | * | 2/1928 | Greenblatt | 401/155 |
| D232,278 S | * | 8/1974 | Gallo | D4/101 |
| 4,294,269 A | * | 10/1981 | Kyte | 132/309 |
| 4,845,796 A | * | 7/1989 | Mosley | 15/23 |
| 5,040,553 A | | 8/1991 | Londono et al. | |
| 5,044,386 A | * | 9/1991 | Nelson | 132/309 |
| D354,625 S | * | 1/1995 | Weissmann | D4/109 |
| 5,388,599 A | | 2/1995 | Yen | |
| 6,325,076 B1 | | 12/2001 | Ramirez | |
| 6,582,224 B1 | * | 6/2003 | Lilien et al. | 433/1 |
| 7,156,107 B2 | * | 1/2007 | Hsu | 132/309 |

* cited by examiner

*Primary Examiner*—Todd E. Manahan
(74) *Attorney, Agent, or Firm*—Crossley Patent Law; Mark A. Crossley

(57) ABSTRACT

A portable compact dental hygiene kit, comprising a cylindrical case threadably receiving a handle end on one end, a cap end on the opposite end of the case, a removable toothbrush with 360 degree bristles fitting the handle end and removably extending into a toothpaste reservoir within the case, a restrictor proximal to the toothpaste reservoir whereby toothbrush removal retains a metered dose of toothpaste upon the toothbrush, a removable spool of dental floss disposed within the cap end, a removable spool shaft retaining the spool, a floss outlet and cutter within the cap end.

16 Claims, 4 Drawing Sheets

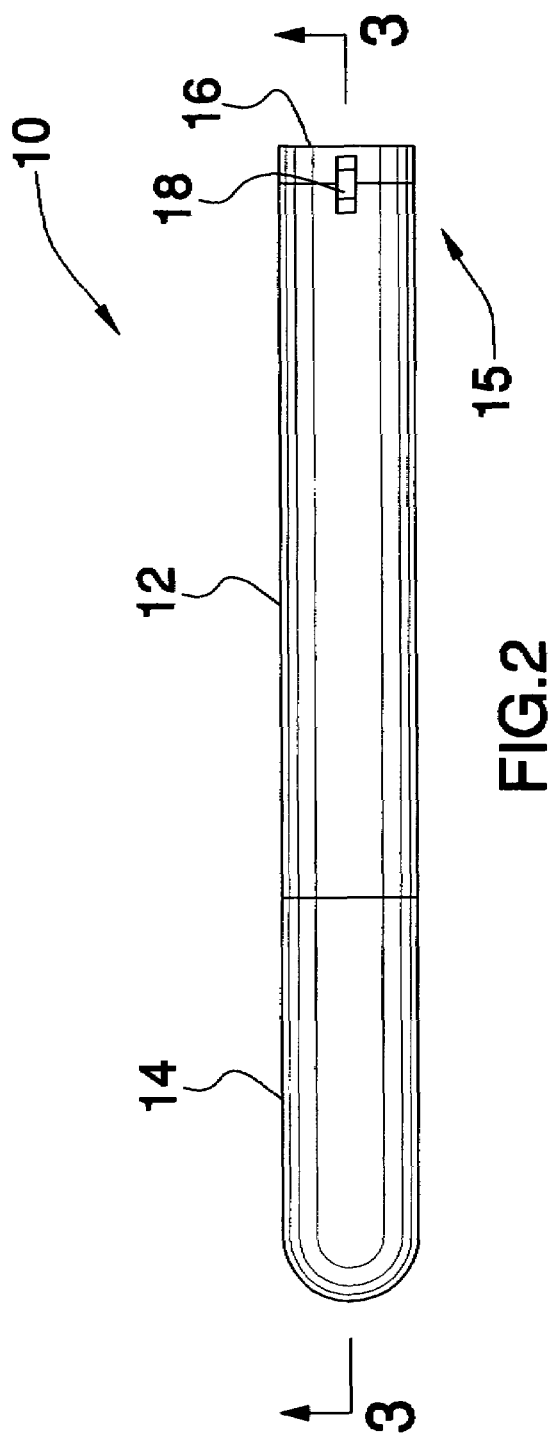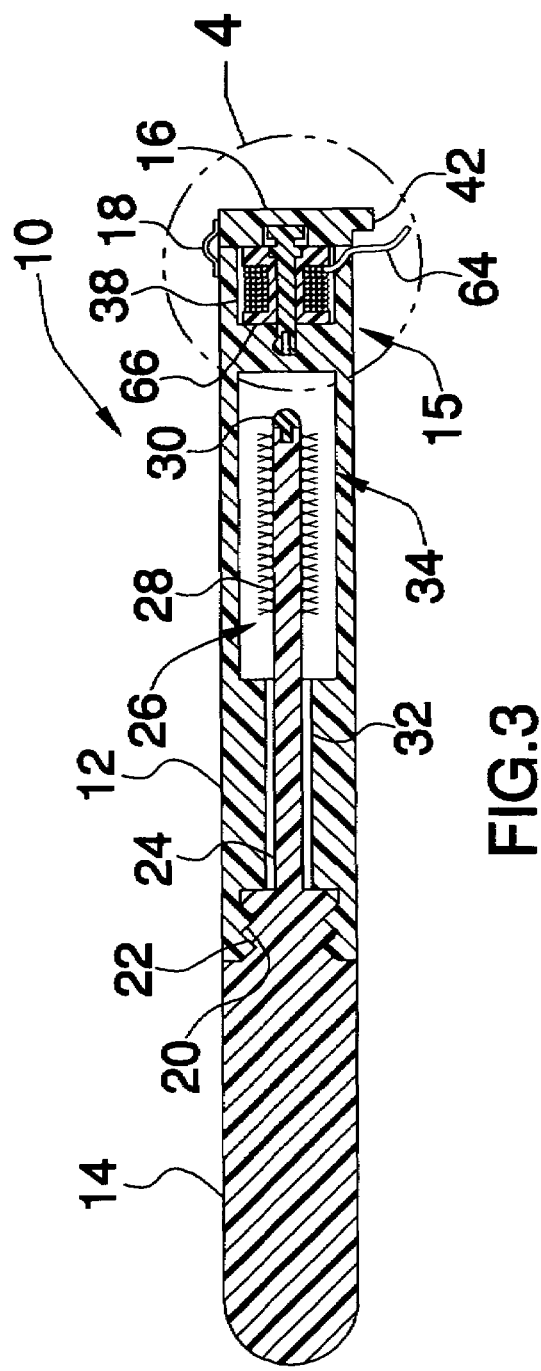

PORTABLE COMPACT DENTAL HYGIENE KIT

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Over time there have been repeated attempts to provide compact tooth brush kits. The need for such has increased with a more mobile society. Meals away from home, travel, and hurried schedules have increased the desire and need for more portability in dental hygiene. Addressing issues such as halitosis, cavities, and gingivitis are routine concerns. A complete dental hygiene kit is needed. Additionally, any device which fulfills the needs raised by these issues and concerns must address the particular concerns of child dental health as well. Children, for example, have a difficult time positioning a toothbrush such that the brush contacts their teeth. The present invention solves these problems, concerns, and more.

FIELD OF THE INVENTION

The invention relates to dental hygiene and more specifically to a complete compact dental hygiene kit.

SUMMARY OF THE INVENTION

The general purpose of the compact dental hygiene kit, described subsequently in greater detail, is to provide a compact dental hygiene kit which has many novel features that result in an improved compact dental hygiene kit which is not anticipated, rendered obvious, suggested, or even implied by prior art, either alone or in combination thereof.

To accomplish this, the invention comprises a cylindrical case. The case is bounded on one end by a removable handle. The opposite end of the case is comprised of cap end. The cap end is abutted by a cap. The cap pivotally opens via a hinge. The hinge is tensioned. The hinge thereby causes the cap to remain in closed position until a desired opening. A tab on the edge of the cap provides for ease of opening.

A handle is firmly fitted within and against cylindrical case of invention. The handle screws into the case by way of male thread on the handle and female thread within the end of the case.

The handle is further comprised of a neck. A toothbrush is disposed on the neck at the end of the neck opposite the handle. The toothbrush is comprised of bristles that surround the circumference of the toothbrush in a full 360 degrees. The end of the toothbrush is further comprised of a rubber tip. The tip is typically used to massage gums. The cylindrical case is further comprised of an interior toothpaste reservoir. The toothpaste reservoir holds toothpaste. The reservoir is refilled as chosen. A restriction is between the toothpaste reservoir and the female thread of the case. The restriction is larger in diameter than the neck of handle. The restriction is smaller in diameter than the toothpaste reservoir. As the bristles of the toothbrush pass through the restriction, excess toothpaste is shed from the bristles and retained within the toothpaste reservoir. The bristles thereby hold a metered dose of toothpaste for each use.

The end of the case opposite the female thread is the cap end of the case. The cap end comprises a spool well. The spool well removably houses a floss spool. The spool holds floss. The cap covers the spool well. The hinge tensionally retains the cap against the cap end. The cap is further comprised of a tab on the outer edge of the cap. The tab aids in opening the cap.

The cap end is abutted by the closed cap. The cap is held closed by the tensioned hinge. The hinge is affixed to the outside of the cap and the cap end. The cap is further comprised of a head gap on the interior of the cap. The head gap freely receives a pull head of the spool shaft. The cap end is proximal to but not adjoining the toothpaste reservoir of the case. The cap end further comprises the spool well.

A shaft receiver is proximal to but separated from the toothpaste reservoir within the cap end. The shaft receiver is further comprised of a detent receptacle. The detent receptacle is disposed upwardly at the end of the shaft receptacle. The spool well removably houses a floss spool. The floss spool holds floss. The end of the spool well is further comprised of a floss outlet. The floss outlet is immediately adjacent to the cap. The floss outlet is further comprised of a floss cutter. Pulling floss backwardly along the length of the case affects cutting the floss. The spool shaft freely holds the floss spool such that the spool can turn and release the floss from the floss outlet. The spool shaft is further comprised of a shoulder. The shoulder of the shaft is removably received by a shoulder housing of the spool. The spool shaft is further comprised of a recession. The recession is immediately adjacent to the shoulder of the shaft. A pull head is immediately outwardly adjacent to the recession. The pull head is of greater circumference than the recession of the shaft. The recession and the pull head thereby provide a grip for removal of the shaft from the shaft receiver. A detent knob is disposed on the end of the spool shaft that is opposite the pull head. The end of the shaft with the detent knob is also comprised of a compression gap. The compression gap provides for compression of the detent ball such that the shaft can be removed.

The portable compact dental hygiene kit provides for virtually all dental care needed in travel. The toothbrush, replaceable floss, toothpaste reservoir, and rubber massage tip comprise a complete kit in a highly portable and space efficient package. The toothbrush is functional when rotated in any rotational position, thereby negating the need to position bristles in any specified direction.

This feature is especially useful for children who have a difficult time positioning bristles properly against teeth. The kit is made of typical materials known in the art. Further examples of the kit are even more inexpensively produced such that they are disposable when out of toothpaste or floss.

Thus has been broadly outlined the more important features of the compact dental hygiene kit so that the detailed description thereof that follows may be better understood and in order that the present contribution to the art may be better appreciated.

Numerous objects, features and advantages of the compact dental hygiene kit will be readily apparent to those of ordinary skill in the art upon reading the following detailed description of presently preferred, but nonetheless illustrative, examples of the compact dental hygiene kit when taken in conjunction with the accompanying drawings. In this respect, before explaining the current examples of the compact dental hygiene kit in detail, it is to be understood that the invention is not limited in its application to the details of construction and arrangements of the components set forth in the following description or illustration. The invention is capable of other examples and of being practiced and carried out in various ways. It is also to be understood that the phraseology and terminology employed herein are for purposes of description and should not be regarded as limiting.

Those skilled in the art will appreciate that the conception upon which this disclosure is based may readily be utilized as a basis for the design of other structures, methods and systems for carrying out the several purposes of the compact dental hygiene kit. It is therefore important that the claims be regarded as including such equivalent constructions insofar as they do not depart from the spirit and scope of the present invention.

Objects of the compact dental hygiene kit, along with various novel features that characterize the invention are particularly pointed out in the claims forming a part of this disclosure. For better understanding of the compact dental hygiene kit, its operating advantages and specific objects attained by its uses, refer to the accompanying drawings and description.

BRIEF DESCRIPTION OF THE DRAWINGS

FIG. 2 is a top plan view of the closed invention case.

FIG. 3 is a cross section view of FIG. 2 taken along the line 3-3.

DETAILED DESCRIPTION OF THE DRAWINGS

With reference now to the drawings, and in particular Figures through 5 thereof, example of the compact dental hygiene kit employing the principles and concepts of the present invention and generally designated by the reference number 10 will be described.

Figure 1:
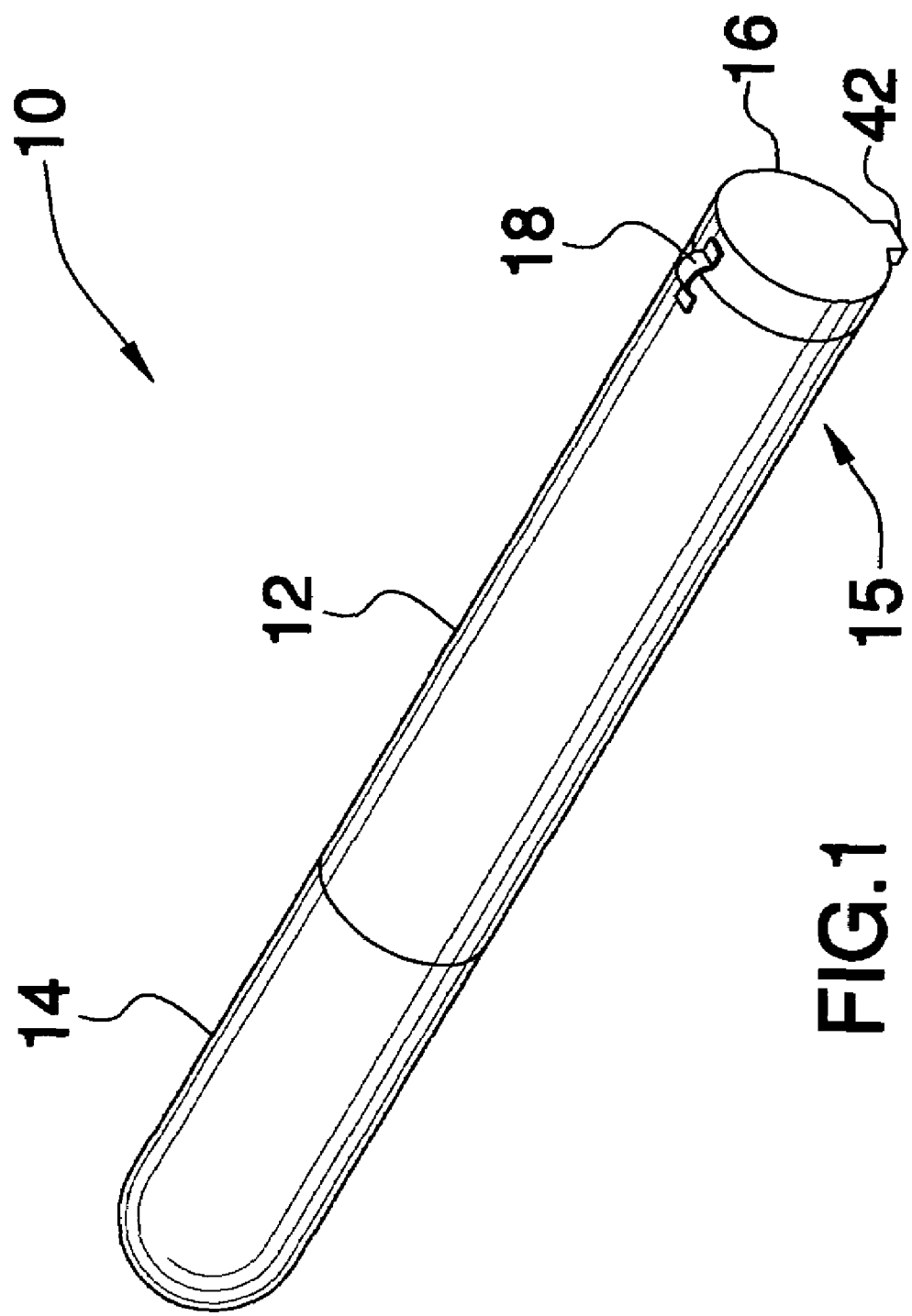
FIG. 1 is a perspective view of the closed invention case.

Referring to FIG. 1, the invention 10 comprises a cylindrical case 12. The case 12 is bounded on one end by removable handle 14. The opposite end of the case 12 is comprised of cap end 15. The cap end 15 is abutted by the cap 16. The cap 16 pivotally opens via hinge 18. The hinge 18 is tensioned. The hinge 18 thereby causes cap 16 to remain in closed position until desired opening. The tab 42 on the edge of the cap 16 provides for ease of opening the cap 16.

Referring to FIG. 2, the handle 14 is firmly fitted within and against cylindrical case 12 of invention 10. The cap 16 is closed against cap end 15. The tensioned hinge 18 retains closed position of cap 16.

Referring to FIG. 3, the handle 14 is comprised of male thread 22. The case 12 is comprised of female thread 20. The male thread 22 thereby screws into the female thread 20 to secure handle 14 within the case 12. The handle 14 is further comprised of a neck 24. The toothbrush 26 is disposed on the neck 24 at the end of the neck 24 opposite the handle 14.

The toothbrush 26 is comprised of bristles 28 that surround the circumference of the toothbrush 26 in a full 360 degrees. The end of the toothbrush 26 is further comprised of a rubber tip 30. The cylindrical case 12 is further comprised of an interior toothpaste reservoir 34. The toothpaste reservoir 34 holds toothpaste (not shown). A restriction 32 is between the toothpaste reservoir 34 and the female thread 20 of the case 12. The restriction 32 is larger in diameter than the neck 24 of handle 14. The restriction 32 is smaller in diameter than the toothpaste reservoir 34. The end of the case 12 opposite the female thread 20 is the cap end 15. The cap end 15 comprises a spool well 38. The spool well 38 removably houses a floss spool 66. The spool 66 holds floss 64. The cap 16 covers the spool well 38. The hinge 18 tensionally retains the cap 16 against the cap end 15. The cap 16 is further comprised of the tab 42. The tab 42 aids in opening the cap 16.

Figure 4:
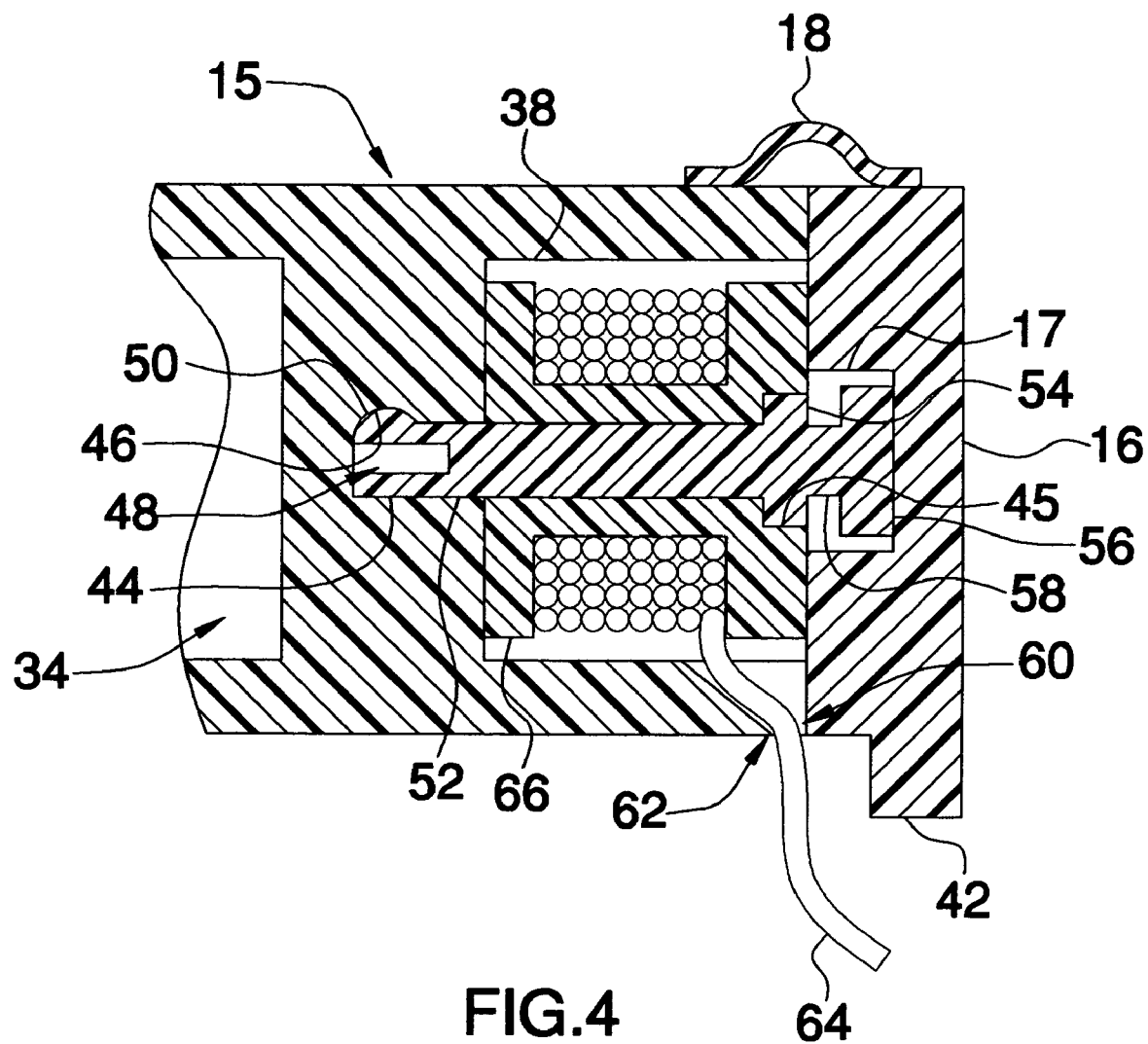
FIG. 4 is a view of the flip snap end of the invention taken from circle 4 of FIG. 3.

Referring to FIG. 4, the cap end 15 of the invention 10 is abutted by the closed cap 16. The cap 16 is held closed by the tensioned hinge 18. The hinge 18 is affixed to the outside of the cap 16 and the cap end 15. The cap 16 is further comprised of the head gap 17. The head gap 17 freely receives the pull head 56 of the spool shaft 52. The cap end 15 is proximal to the toothpaste reservoir 34 of the case 12. The cap end 15 further comprises the spool well 38. The shaft receiver 44 is proximal to but separated from the toothpaste reservoir 34 within the cap end 15. The shaft receiver 44 is further comprised of the detent receptacle 46. The detent receptacle 46 is disposed at the end of the shaft receptacle 44. The spool well 38 removably houses the floss spool 66. The floss spool 66 holds floss 64. The end of the spool well 38 is further comprised of the floss outlet 60.

The floss outlet 60 is immediately adjacent to the cap 16. The floss outlet 60 is further comprised of the floss cutter 62. The spool shaft 52 freely holds the floss spool 66 such that the spool 66 can turn (not shown) and release the floss 64 from the floss outlet 60. The spool shaft 52 is further comprised of the shoulder 54. The shoulder 54 of the shaft 52 is removably received by the shoulder housing 45 of the spool 66. The spool shaft 52 is further comprised of the recession 58. The recession 58 is immediately adjacent to the shoulder 54 of the shaft 52. The pull head 56 is immediately outwardly adjacent to the recession 58. The recession 58 and the pull head 56 provide a grip for removal of the shaft 52 from the shaft receiver 44. The detent knob 50 is disposed on the end of the spool shaft 52 that is opposite the pull head 56. The end of the shaft 52 with the detent knob 50 is also comprised of the compression gap 48. The compression gap 48 provides for compression of the detent ball 50 such that the shaft 52 can be removed.

Figure 5:
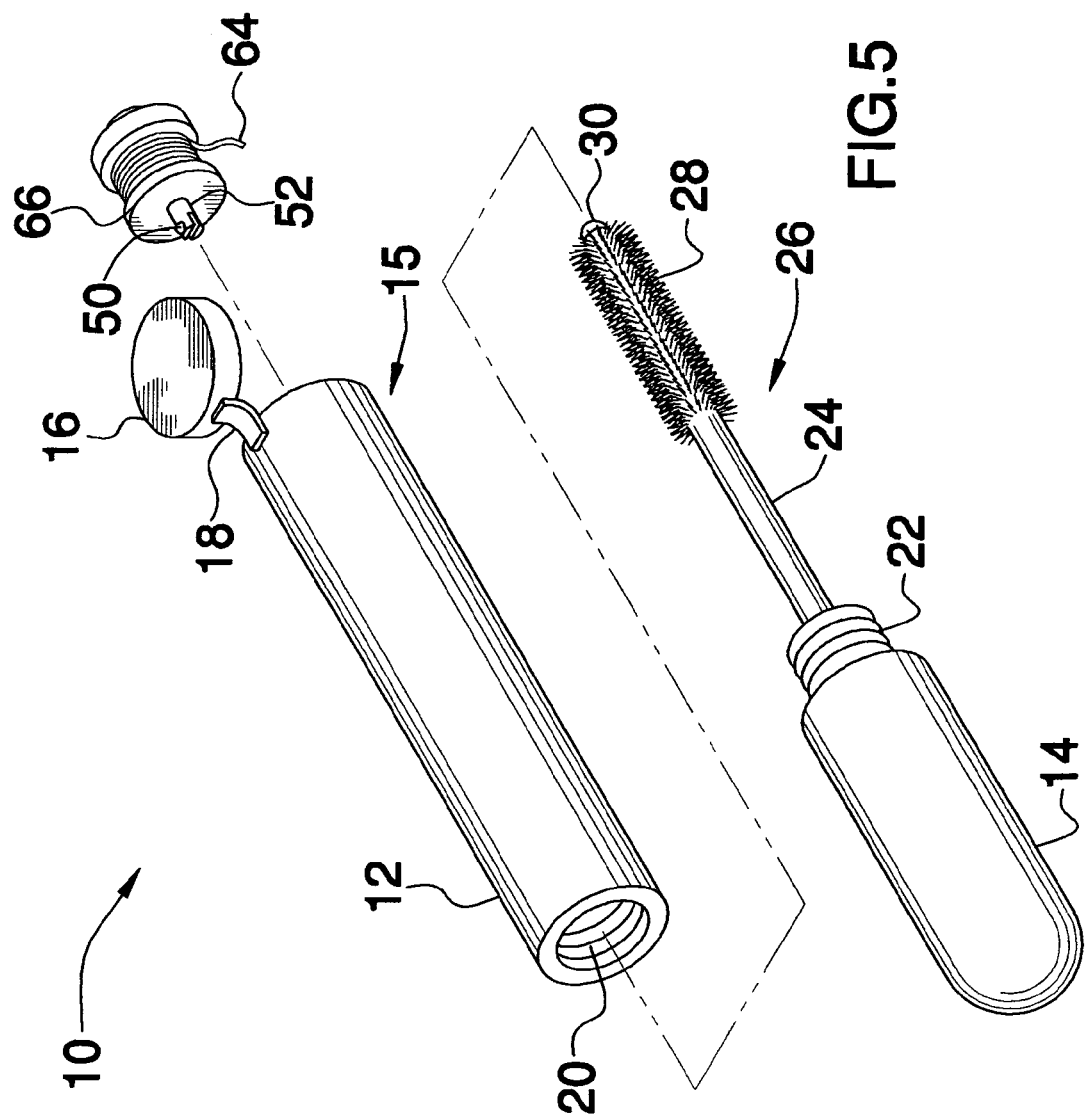
FIG. 5 is a perspective view of the fully opened case of the invention.

Referring to FIG. 5, the male thread 22 of the handle 14 is unscrewed from the female thread 20 of the case 12. Bristles 28 of the toothbrush 26 are arranged in a full 360 degrees around the toothbrush 26. The rubber tip 30 is on the end of the toothbrush 26. The cap 16 is pivotally opened from the cap end 15. The tension of the hinge 18 is momentarily overcome. The floss spool 66 containing floss 64 is removed from the cap end 15.

In use, a user (not shown) grasps handle 14 and rotates to remove the toothbrush 26 from the case 12. In removal, the toothbrush bristles 28 must pass through the restriction 32 of the case 12. The restriction thereby removes excess toothpaste (not shown) from the bristles 28.

The size of the restriction 32 provides for a metered dose of toothpaste to remain on the bristles 28. A user brushes teeth (not shown) with the toothbrush 26. The toothbrush 26 is functional when rotated in any rotational position, thereby negating the need to position bristles 28 in any specified direction. The toothpaste reservoir 34 is refilled as needed by squeezing toothpaste into the reservoir 34 through the female thread 20 and the restriction 32. The toothbrush 26 is re-inserted into the toothpaste reservoir 34 and the male thread 22 is rotatably secured within the female thread 20. As chosen, the floss 64 is used either before or after using the toothbrush 26. The floss 64 is pulled from the floss opening 60. The floss 64 is pulled back along the length of the case 12 such that the floss cutter 62 cuts floss 64 at a desired length. When empty, the spool well 38 is refilled with a floss spool 66 with floss 64. The tab 42 is used to pull the cap 16 pivotally away from the cap end 15. The tension of the hinge 18 is momentarily overcome. The pull head 56 of the spool shaft 52 is grasped. The pull head is pulled outwardly in order to remove the spool shaft 52 from the shaft receiver 44. The compression gap 38 of the spool shaft 52 is momentarily narrowed. Narrowing of the compression gap 38 allows the removal of the detent knob 50 from the detent receptacle 46. The spool shaft 52 is removed from the floss spool 66. A new floss spool 66 is added. The above procedure is reversed for installation of the new floss spool 66.

With respect to the above description then, it is to be realized that the optimum dimensional relationships for the parts of the compact dental hygiene kit, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Directional terms such as "front", "back", "in", "out", "downward", "upper", "lower", and the like may have been used in the description. These terms are applicable to the examples shown and described in conjunction with the drawings. These terms are merely used for the purpose of description in connection with the drawings and do not necessarily apply to the position in which the present invention may be used.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A portable compact dental hygiene kit, comprising:
   a cylindrical case having a length, one end, and an opposite end;
   a toothpaste reservoir within the case;
   a removable handle on the one end of the case;
   a neck on an interior end of the handle;
   a toothbrush on an end of the neck;
   a plurality of bristles disposed around an entire 360 degree circumference of the toothbrush;
   a cap end on the opposite end of the case;
   a spool well within the cap end;
   a shaft receiver medially proximal to the spool well, the shaft receiver having a detent receptacle;
   a spool shaft removably disposed within the cap end, the shaft coplanar to the length of the case;
   a pull head on one end of the spool shaft;
   a detent knob on an opposite end of the spool shaft;
   such that the spool shaft with the detent knob are removably retained by the shaft receiver and detent receptacle;
   a spool of dental floss removably received by the spool shaft;
   such that the spool of dental floss is removably held within the spool well by the spool shaft;
   a cap on the cap end of the cylindrical case;
   a hinge attaching the cap to the cap end of the case;
   a head gap within an interior of the cap;
   such that the cap freely surrounds the pull head of the spool shaft.

2. The invention in claim 1 wherein the spool shaft further comprises a recession immediately adjacent to the pull head;
   a shoulder immediately adjacent to the recession;
   such that the pull head is accessible in removing the spool shaft from the cap end of the case.

3. The invention in claim 2 wherein the spool reservoir is further comprised of a floss outlet;
   a floss cutter within the floss outlet.

4. The invention in claim 3 wherein the floss cutter is disposed immediately proximal to the cap of the cap end.

5. The invention in claim 4 wherein the hinge is flexibly tensioned.

6. The invention in claim 5 wherein the removable handle end of the cylindrical case comprises a male thread;
   the case further comprised of a female thread;
   such that the handle end is threadably received by the case.

7. The invention in claim 6 wherein the female thread of the case and the toothpaste reservoir of the case are separated by a restriction;
   the restriction having a diameter less than the toothpaste reservoir;
   the restriction having a diameter greater than the handle neck;
   such that removal of the toothbrush retains a metered dose of toothpaste upon the bristles of the toothbrush.

8. The invention in claim 7 wherein the toothbrush end of the neck is tipped by rubber.

9. A portable compact dental hygiene kit, comprising:
   a cylindrical case having a length;
   a female threaded end of the case;
   an opposite cap end of the case;
   a toothpaste reservoir within the case;
   a restriction between the toothpaste reservoir and the threaded end of the case;
   a threaded removable handle fitting the threaded end of the case;
   a neck on an interior end of the handle;
   a toothbrush on an end of the neck;
   bristles disposed around an entire 360 degree circumference of the toothbrush;
   such that removal of the toothbrush retains a metered dose of toothpaste upon the bristles;
   a spool well within the cap end of the case;
   a shaft receiver medially proximal to the spool well, the shaft receiver having a detent receptacle;
   a spool shaft removably disposed within the cap end, the shaft coplanar to the length of the case;
   a pull head on one end of the spool shaft;
   a detent knob on an opposite end of the spool shaft;
   a compression gap within the end of the shaft comprising the detent knob,
   whereby the spool shaft with the detent knob are removably retained by the shaft receiver and detent receptacle, the compression gap aiding in removal of the detent knob of the spool shaft;

a spool of dental floss removably received by the spool shaft;

such that the spool of dental floss is removably held within the spool well by the spool shaft;

a cap on the cap end of the cylindrical case;

a hinge attaching the cap to the cap end of the case;

a head gap within an interior of the cap;

such that the cap freely surrounds the pull head of the spool shaft.

10. The invention in claim 9 wherein the spool reservoir is further comprised of a floss outlet;

a floss cutter within the floss outlet.

11. The invention in claim 10 wherein the floss cutter is disposed immediately proximal to the cap of the cap end.

12. The invention in claim 11 wherein the hinge is flexibly tensioned.

13. The invention in claim 12 wherein the toothbrush end of the neck is tipped by rubber.

14. A portable compact dental hygiene kit, comprising:

a cylindrical case having a length;

a female threaded end of the case;

an opposite cap end of the case;

a toothpaste reservoir within the case;

a restriction between the toothpaste reservoir and the threaded end of the case;

a threaded removable handle fitting the threaded end of the case;

a neck on an interior end of the handle;

a toothbrush on an end of the neck;

bristles disposed around an entire 360 degree circumference of the toothbrush;

such that removal of the toothbrush retains a metered dose of toothpaste upon the bristles;

a spool well within the cap end of the case;

a floss outlet within the spool well, the floss outlet immediately adjacent to the cap end;

a floss cutter within the floss outlet;

a shaft receiver medially proximal to the spool well, the shaft receiver having a detent receptacle;

a spool shaft removably disposed within the cap end, the spool shaft coplanar to the length of the case;

a pull head on one end of the spool shaft;

a recession immediately adjacent to the pull head;

a shoulder immediately adjacent to the recession;

such that the pull head is accessible in removing the spool shaft from the cap end of the case;

a detent knob on an opposite end of the spool shaft;

such that the spool shaft with the detent knob are removably retained by the shaft receiver and detent receptacle;

a spool of dental floss removably received by the spool shaft;

a shoulder housing on the cap end of the spool, the shoulder housing for removable receipt of the shoulder of the spool shaft;

such that the spool of dental floss is removably held within the spool well by the spool shaft;

a cap on the cap end of the cylindrical case;

a cap tab on an outer edge of the cap;

a hinge attaching the cap to the cap end of the case;

a head gap within an interior of the cap;

such that the cap freely surrounds the pull head of the spool shaft.

15. The invention in claim 14 wherein the hinge is flexibly tensioned.

16. The invention in claim 15 wherein the toothbrush end of the neck is tipped by rubber.

* * * * *